(12) United States Patent
White et al.

(10) Patent No.: US 11,370,737 B2
(45) Date of Patent: Jun. 28, 2022

(54) CO-FEEDING ETHYLENE WITH ALLYL ALCOHOL IN HYDROFORMYLATION TO MAKE 1,4-BUTANEDIOL AND N-PROPANOL

(71) Applicant: Lyondell Chemical Technology, L.P., Houston, TX (US)

(72) Inventors: Daniel F. White, Houston, TX (US); Beaven S. Mandimutsira, Sugar Land, TX (US); Roberto Alvarez, Houston, TX (US)

(73) Assignee: Lyondell Chemical Technology, L.P., Houston, TX (US)

(*) Notice: Subject to any disclaimer, the term of this patent is extended or adjusted under 35 U.S.C. 154(b) by 0 days.

(21) Appl. No.: 17/480,265

(22) Filed: Sep. 21, 2021

(65) Prior Publication Data

US 2022/0098138 A1 Mar. 31, 2022

Related U.S. Application Data

(60) Provisional application No. 63/083,615, filed on Sep. 25, 2020.

(51) Int. Cl.

| | | |
|---|---|---|
| *C07C 45/50* | (2006.01) | |
| *C07C 29/00* | (2006.01) | |
| *B01J 31/00* | (2006.01) | |
| *B01J 31/24* | (2006.01) | |
| *C07C 29/158* | (2006.01) | |

(52) U.S. Cl.
CPC ......... *C07C 45/505* (2013.01); *B01J 31/2409* (2013.01); *C07C 29/158* (2013.01); *B01J 2231/321* (2013.01); *B01J 2531/822* (2013.01)

(58) Field of Classification Search
CPC ..... C07C 45/50; C07C 45/505; C07C 29/158; B01J 31/2409; B01J 2231/321
See application file for complete search history.

(56) References Cited

U.S. PATENT DOCUMENTS

| | | |
|---|---|---|
| 4,306,087 A | 12/1981 | Matsumoto et al. |
| 5,237,106 A * | 8/1993 | Babin ..................... C07C 45/50 568/454 |
| 6,225,509 B1 | 5/2001 | Dubner et al. |
| 7,271,295 B1 | 9/2007 | White et al. |
| 7,279,606 B1 | 10/2007 | White |
| 7,294,602 B1 | 11/2007 | White |
| 9,795,952 B2 | 10/2017 | Diebolt et al. |
| 2016/0068458 A1 | 3/2016 | Mandimutsira et al. |

FOREIGN PATENT DOCUMENTS

WO 2008121194 A1 10/2008

OTHER PUBLICATIONS

The International Search Report and the Written Opinion for PCT/US2021/051186 dated Dec. 21, 2021.

* cited by examiner

*Primary Examiner* — Sikarl A Witherspoon

(57) ABSTRACT

A process of co-feeding gaseous ethylene with liquid allyl alcohol in the presence of a catalyst to produce 1,4-butanediol and n-propanol may include: introducing a gaseous mixture of ethylene, carbon monoxide and hydrogen into a reactor in the presence of a hydroformylation catalyst in a solvent; introducing liquid allyl alcohol (AA) into the reactor; and carrying out hydroformylation reaction at a temperature between 50 and 100° C. to obtain hydroformylation products.

20 Claims, 5 Drawing Sheets

CO-FEEDING ETHYLENE WITH ALLYL ALCOHOL IN HYDROFORMYLATION TO MAKE 1,4-BUTANEDIOL AND N-PROPANOL

CROSS-REFERENCED TO RELATED APPLICATIONS

This application claims the benefit of priority to U.S. Provisional Patent Application No. 63/083,615, filed on Sep. 25, 2020, which is incorporated herein by reference in its entirely

TECHNICAL FIELD

The disclosure relates to a process of producing 1,4-butanediol (BDO) and its branched co-product, 2-methyl-1,3-propanediol (MPDiol®) as well as n-propanol (n-Pr) by co-feeding gaseous ethylene with liquid allyl alcohol in the hydroformylation process, and more particularly to a process of producing n-propanol and BDO by co-feeding the gaseous ethylene with liquid allyl alcohol in a homogenous reaction in the presence of hydroformylation catalyst.

BACKGROUND

Conventionally 1,4-butanediol (BDO) is manufactured using propylene oxide (PO) as a starting material. PO is first isomerized to allyl alcohol (AA), followed by hydroformylation with syngas, $H_2$+CO to obtain 4-hydroxybutyraldehyde (HBA) which is then hydrogenated to 1,4-butanediol. See, for example, U.S. Pat. No. 4,215,077.

Hydroformylation is a process in which an alkene is reacted with carbon monoxide and hydrogen to form an aldehyde. This process is used in the chemical industry to produce compounds such as propionaldehyde and butyraldehyde from the simple olefins, for example ethylene and propylene.

In ethylene hydroformylation, the propionaldehyde (PA) product is distilled from the catalyst solution prior to hydrogenation to produce n-propanol, see for example, U.S. Pat. No. 4,262,142. A typical hydroformylation process involves catalysts such as Rh-phosphite complexes and requires high process temperature in the range of 100 to 145° C. The high temperature increases the cost of production.

Another process is hydroformylation of activated olefins such as allyl alcohol to produce the hydroxy aldehydes, including 4-hydroxybutyraldehyde and 3-hydroxy-2-methylpropionaldehyde (HMPA). In this process, the hydroxy aldehydes in the toluene catalyst solution are extracted by water prior to hydrogenation over a sponge nickel catalyst. The remaining catalyst solution is then recycled back to the hydroformylation process.

Hydroformylation mechanisms are different for gaseous starting material such as ethylene and liquids such as allyl alcohol. The process control to combine the two hydroformylation reactions and maintain a linear-to-branched ratio and effective separation of products from the recycle catalyst solution can be difficult. Therefore, there is still the need to effectively produce 1,4-butanediol and n-propanol while maintaining high linear-to-branched C4-diols ratio and efficiently recycling the catalyst.

SUMMARY OF THE DISCLOSURE

This disclosure provides a process that produces propanol and additionally 1,4-butanediol and 2-methyl-1,3-propanediol. The process of this disclosure relates to co-feeding gaseous ethylene with liquid allyl alcohol, along with carbon monoxide and hydrogen in the presence of a solvent and a hydroformylation catalyst to produce linear 4-hydroxybutyraldehyde, branched isomer 3-hydroxy-2-methyl-propionaldehyde and propionaldehyde. The hydroformylation catalyst comprises a rhodium phosphine complex. After hydroformylation is completed, the reaction products undergo water extraction to separate HBA/HMPA/PA from the hydroformylation catalyst/solvent, where the catalyst/solvent will be recycled back to the hydroformylation reaction. The aqueous aldehydes solution then undergoes hydrogenation in the presence of a nickel catalyst, where HBA and HMPA are converted to BDO and MPDiol®, respectively, while propionaldehyde is converted to n-propanol.

The linear (HBA) to branched (HMPA) ratio is maintained at 10:1 or higher, with increased production of PA that is suitable for further processing of these products. The significantly lower reaction temperature (approximately 65° C.) saves energy compared to a reaction temperature at 100-145° C. Potential savings also are realized in preservation of phosphine ligands which degrade more as reaction temperature increases above 110° C.

According to an aspect of this disclosure, the molar ratio of ethylene to allyl alcohol ranges from 1:3 to 1:7. In one embodiment, the molar ratio of ethylene to allyl alcohol ranges from 1:4 to 1:5.

According to an aspect of this disclosure, the amount of allyl alcohol used in the hydroformylation reaction is 5-40 wt. % in the solvent.

According to an aspect of this disclosure, the molar ratio of ethylene:carbon monoxide:hydrogen is (0.18-0.35):(2.7-4.1):(5-7). In one embodiment, the molar ratio of ethylene:carbon monoxide:hydrogen is about 1:13:22.

According to an aspect of this disclosure, the gaseous mixture is introduced at an elevated pressure ranging from about 137.9 kPa to about 1378.95 kPa. In one embodiment, the gaseous mixture is introduced at a pressure ranging from about 689.48 kPa to about 1034.21 kPa. In one embodiment, the gaseous mixture is introduced at a pressure ranging from about 896.32 kPa to about 965.27 kPa.

According to an aspect of this disclosure, the hydroformylation catalyst is a mixture of rhodium and a ligand selected from the group consisting of trans-1,2-bis(3,5-trimethylphenylphosphinomethyl)cyclobutane (Ligand A), 1,4-bis(diphenylphosphinobutane) (DPPB), triphenylphosphine (TPP), bidentate biphosphate, and combinations thereof.

According to an aspect of this disclosure, the molar ratio of rhodium to Ligand A ranges from 1:1 to 1:5, or the molar ratio of rhodium to Ligand A is about 1:2.

According to an aspect of this disclosure, the hydroformylation catalyst is a mixture of rhodium, Ligand A, DPPB and TPP, or the molar ratio of rhodium:Ligand A:DPPB:TPP is about 1:2:0.1:2. According to an aspect of this disclosure, the molar ratio of rhodium:Ligand A:DPPB:TPP may be in the range of about 0.8-1.2:1.6-2.4:0.08-0.12:1.6-2.4, wherein each value in the indicated ranges may be independently selected.

According to an aspect of this disclosure, the rhodium is present in an amount of 50 to 500 ppm.

According to an aspect of this disclosure, the reaction temperature is maintained between 50-100° C., or the reaction temperature is maintained between 60-80° C.

According to an aspect of this disclosure, the water-to-feed ratio in the water extraction process ranges from 1:5 to 2:1. According to an aspect of this disclosure, the water-to-feed ratio in the water extraction process ranges from 1.5:4 to 1.5:1. According to an aspect of this disclosure, the water-to-feed ratio in the water extraction process ranges from 3:5 to 1:1. According to an aspect of this disclosure, the water-to-feed ratio in the water extraction process ranges from 1:1 to 2:1. According to an aspect of this disclosure, the water-to-feed ratio in this water extraction process ranges from 1:5 to 1:1. According to an aspect of this disclosure, the water-to-feed ration in the water extraction process ranges from 1:3 to 1:1.

As used herein, the term "inert solvent" refers to solvents that are stable under the reaction condition without decomposition or forming impurities.

As used herein, "hydroformylation" refers to a reaction of adding a formyl group (CHO) and a hydrogen atom to a carbon-carbon double bond of an alkene to produce an aldehyde.

As used herein, "hydroformylation catalyst" refers to a catalyst system that facilitates the hydroformylation reaction at a lower temperature.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed and excludes all additional elements.

The phrase "consisting essentially of" excludes additional material elements but allows the inclusions of non-material elements that do not substantially change the nature of this disclosure.

The following abbreviations are used herein:

| ABBREVIATION | TERM |
|---|---|
| AA | Allyl alcohol |
| BDO | 1,4-butanediol |
| DIOP | 2,3-O-isopropylidene-2,3-dihydroxy-1,4-bis(diphenylphosphino)butane |
| DPPB | 1,4-bis(diphenylphosphino)butane |
| HBA | 4-Hydroxybutyraldehyde |
| HMPA | 3-Hydroxy-2-methylpropionaldehyde |
| MPDiol ® | 2-methyl-1,3-propanediol |
| PA | Propionaldehyde |
| SLH | Standard liter per hour |
| TPP | triphenylphosphine |

DETAILED DESCRIPTION

The disclosure provides a novel method of co-feeding a gaseous mixture of ethylene, carbon monoxide and hydrogen with a liquid phase allyl alcohol in order to perform hydroformylation in the presence of a hydroformylation catalyst in a solvent. The resulting products can be separated from the catalyst/solvent for further process, such as hydrogenation, to eventually produce 1,4-butanediol and n-propanol.

While it is conventional to perform hydroformylation of allyl alcohol to produce 4-hydroxybutyraldehyde followed by hydrogenation to produce 1,4-butanediol, co-feeding gaseous ethylene with allyl alcohol provides a pathway to produce additional products, such as propionaldehyde. However, separating the aldehyde products from the hydroformylation catalyst solution is technically challenging. While the hydroxy aldehydes (products of allyl alcohol hydroformylation) are extracted efficiently in water, propionaldehyde generated from ethylene hydroformylation is collected by distillation from the hydroformylation catalyst solution. See for example U.S. Pat. No. 9,795,952. The temperature for such distillation can be as high as 150° C., at which temperatures phosphine or phosphite ligand/s decomposition could occur, thus deteriorating the hydroformylation catalyst.

Figure 1:
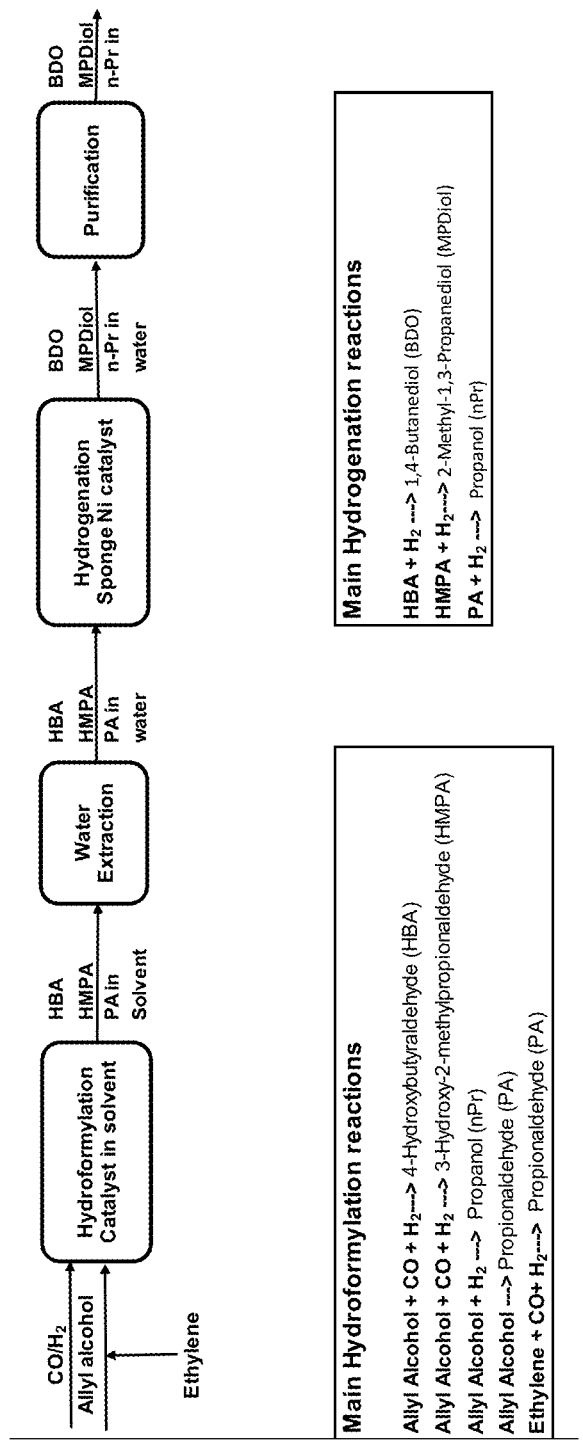
FIG. 1 provides a synthesis strategy of hydroformylation followed by hydrogenation to produce propanol from ethylene co-feed with allyl alcohol.

The process flow is summarized in FIG. 1. Referring to the process flow summarized in FIG. 1, the gas feed that comprises ethylene, carbon monoxide and hydrogen is introduced into a reactor with a liquid feed of allyl alcohol to perform hydroformylation. The process is a homogenous reaction with a gas and liquid substrates and the gaseous feed is mixed with the liquid feed in order to more evenly produce products. The reactor also contains a hydroformylation catalyst, and in one embodiment the hydroformylation catalyst is present in a solvent, such as toluene. The products may comprise HBA, HMPA and PA.

After the hydroformylation reaction is complete, the products along with the hydroformylation catalyst/solvent first undergo water extraction to separate the products from the catalyst/solvent, and the catalyst/solvent can then be recycled back into the hydroformylation reactor. The separated products in water, HBA, HMPA and PA, are moved to the hydrogenation reactor and undergo hydrogenation in the presence of sponge nickel catalyst.

The hydrogenation reaction converts HBA, HMPA and PA into BDO, MPDiol® and n-Pr respectively. The products are further purified to remove water and impurities.

Figure 2:
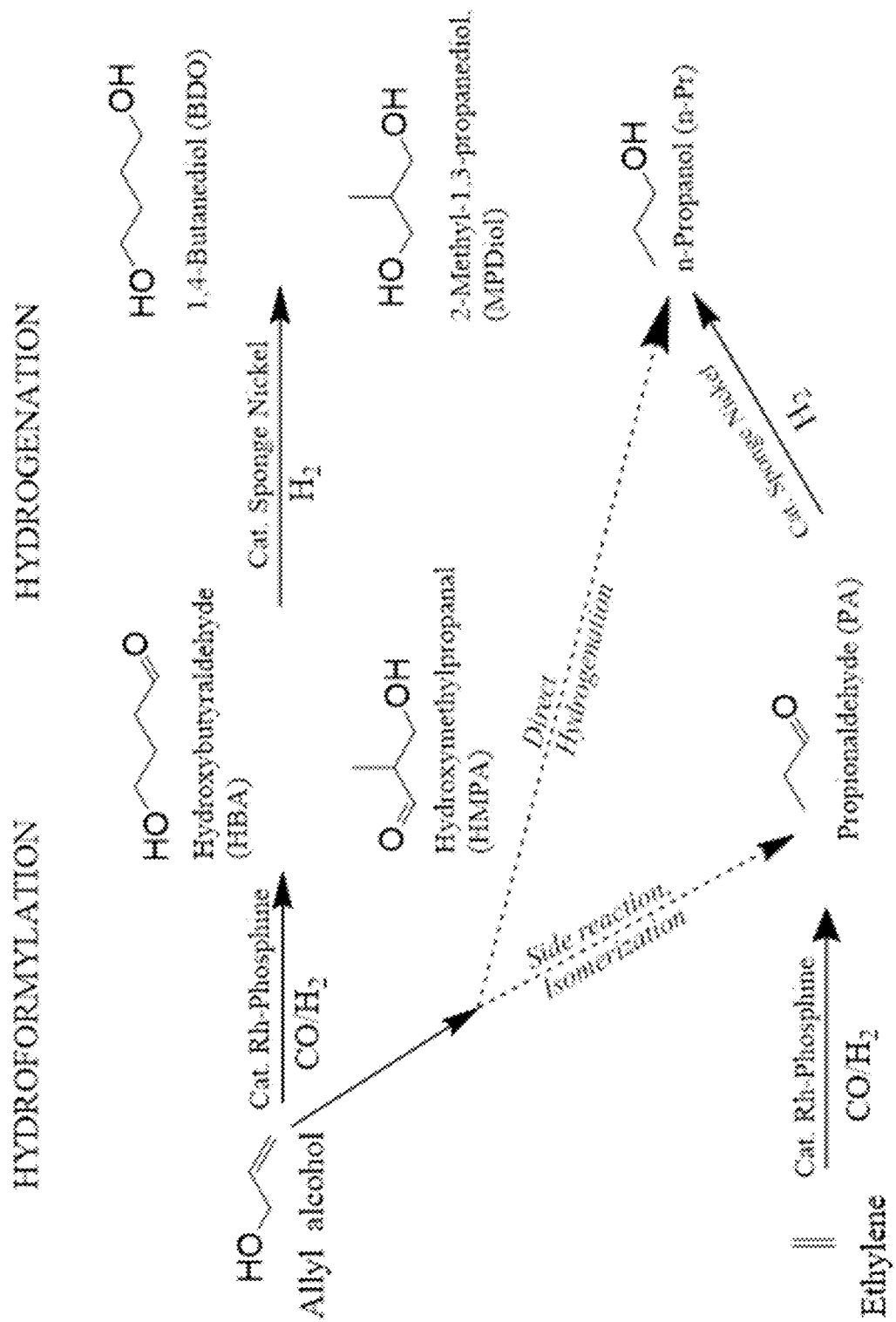
FIG. 2 illustrates the hydroformylation and hydrogenation of allyl alcohol and ethylene.

The chemical synthesis pathway is illustrated in FIG. 2. Referring to FIG. 2, particularly the hydroformylation of allyl alcohol can produce two different isomers, namely the linear 4-hydroxybutyraldehyde and the branched 3-hydroxy-2-methylpropionaldehyde. Each of the isomers will form a diol after hydrogenation and the branched isomer is a lower value product whose production can be minimized.

The starting materials are allyl alcohol and ethylene, along with carbon monoxide and hydrogen in the presence of a hydroformylation catalyst. Allyl alcohol itself is converted to linear 4-hydroxybutyraldehyde and branched 3-hydroxy-2-methylpropanal, (as co-products) while a side reaction would isomerize allyl alcohol to propionaldehyde. Another possible route for allyl alcohol is being directly hydrogenated to form n-propanol.

Gaseous ethylene, on the other hand, undergoes hydroformylation in the presence of the same hydroformylation catalyst to produce propionaldehyde only.

Various hydroformylation catalyst systems can be employed for the hydroformylation reaction. Some such hydroformylation catalysts and processes employ a rhodium complex together with a ligand, such as a phosphine ligand. In these embodiments, the hydroformylation catalyst system comprises a rhodium complex and a phosphine ligand. Such phosphine ligands include trisubstituted phosphines such as triphenyl phosphine. In embodiments, the phosphine ligand can comprise one or more selected from diphosphine ligands, monophosphines, and combinations thereof.

In these embodiments, the hydroformylation catalyst system comprises a rhodium complex and a diphosphine ligand, such as trans-1,2-bis(bis(3,5-di-n-alkylphenyl) phosphinomethyl)cyclobutane, as described, for example, in U.S. Pat. Nos. 7,294,602 and 7,279,606. In these embodiments, the diphosphine ligand comprises trans-1,2-bis(bis(3,5-dimethylphenyl) phosphinomethyl) cyclobutane (also known as trans-1,2-bis[di(3,5-dimethylphenyl) phosphinomethyl] cyclobutane). Trans-1,2-bis(bis(3,5-di-n-alkyl-phenyl)phosphinomethyl) cyclobutane has the chemical structure:

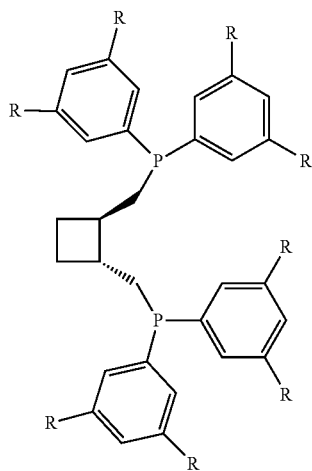

wherein R is an n-alkyl group. In embodiments, R is methyl, ethyl, or propyl. In embodiments, the disphosphine ligand can be trans-1,2-bis(bis(3,5-dimethylphenyl)phosphinomethyl)cyclobutane or trans-1,2-bis(bis(3,5-diethyl-phenyl)phosphinomethyl)cyclobutane, 2,3-O-isopropylidene-2,3-dihydroxy-1,4-bis(diphenylphosphino)butane (DIOP), R,R-xylyl DIOP, trans-1,2-bis(3,4,5-trimethylphenylphosphinomethyl) cyclobutane, or (−)-2,3-O-Isopropylidene-2,3-dihydroxy-1,4-bis(3,5-dimethyl diphenylphosphino)butane. The trans-1,2-bis(bis(3,5-di-n-alkylphenyl) phosphinomethyl) cyclobutane may be prepared by any possible method. For instance, it may be prepared by the reaction of trans-1,2-cyclobutanedimethanol, bis(toluenesulfonate) with lithium di(3,5-di-n-alkylphenyl)phosphine. The ligands and catalyst compositions described herein are commercially available or may be made according to the methods, procedures and processes described in patents and other literature, including U.S. Pat. Nos. 7,271,295, 7,279,606 and WO 2008/121194, each of which is incorporated by reference herein in its entirety for all purposes.

In certain embodiments, the hydroformylation catalyst system further comprises a rhodium complex. Such rhodium complexes contain rhodium attached to ligand groups. In embodiments, the rhodium complex is soluble in the solvent. There are no particular restrictions regarding the choice of ligands attached to the rhodium complex. For example, such ligands include hydrides, carbonyl, substituted and unsubstituted cyclopentadienyls, 2,4-alkanedionates, trialkyl or triaryl phosphines, diphosphines, and mixtures thereof. In embodiments, the ligands attached to the rhodium complex are selected from carbonyl, acetylacetonate (2,4-pentanedionate), triphenylphosphine, and mixtures thereof. Examples of rhodium complexes include, without limitation, (acetylacetonato)dicarbonyl rhodium(I) (also known as dicarbonyl-acetylacetonato-rhodium(I), dicarbonylrhodium (I) 2,4-pentanedionate, $Rh(CO)_2(acac)$, and rhodium(I) dicarbonyl acetylacetonate) and tris(triphenylphosphine) rhodium carbonyl hydride.

The rhodium complex can be pre-associated with the phosphine (e.g., trans-1,2-bis(bis(3,5-di-n-alkylphenyl) phosphinomethyl)cyclobutane) prior to use in the hydroformylation reaction such that the [bis(bis(3,5-di-n-alkylphenyl)-phosphinomethyl)cyclobutane] ligand forms part of the rhodium complex, or it can be added separately. However, in certain embodiments, the rhodium complex is added separately from the phosphine ligand (e.g., the trans-1,2-bis(bis(3,5-di-n-alkylphenyl)phosphinomethyl)cyclobutane). In certain embodiments, the molar ratio of the phosphine ligand:rhodium complex (e.g., the trans-1,2-bis(bis(3,5-di-n-alkylphenyl)-phosphinomethyl) cyclobutane: rhodium complex) can be in the range of 0.5:1 to 5:1.

In embodiments, the hydroformylation catalyst system comprises a rhodium complex and one or more diphosphine ligands, the rhodium complex comprises $Rh(CO)_2(acac)$, and the molar ratio of $Rh(CO)_2(acac)$ to the diphosphine ligands is in the range of from 0.1:1 to 1:5, from 0.9:1.5 to 1:3, or from 1:1.9 to 1:2.1.

In certain embodiments, the hydroformylation catalyst system may additionally comprise an auxiliary ligand, such that the hydroformylation is further performed in the presence of the auxiliary ligand which is added to the catalyst solution. In certain embodiments, the auxiliary ligand comprises a monophosphine.

In certain embodiments, the monophosphine compound is in addition to any phosphine ligand that may be associated with the rhodium complex. In certain embodiments, the monophosphine compound may be a trisubstituted phosphine that is represented by the formula:

$(R^1)_3P$, wherein $R^1$ is an alkyl or aryl group. Aliphatic $R^1$ groups include methyl, ethyl, n-butyl, sec-butyl, octyl, and/or decyl. Aromatic $R^1$ groups include phenyl, tolyl, and/or naphthyl. The $R^1$ groups may be the same or different. In some embodiments, the monophosphine is a trisubstituted aryl phosphine. In other embodiments, the monophosphine may be triphenylphosphine. In other embodiments, the monophosphine is triphenyl phosphine.

In certain embodiments, the hydroformylation catalyst system comprises a diphosphine ligand and a monophosphine, and the monophosphine is present such that a ratio of the diphosphine to the monophosphine is in ranges from 1:1 to 1:3, from 1:1.2 to 1:2, or from 1:1.4 to 1:1.6.

Hydroformylation may be performed in the presence of a hydroformylation reaction solvent. Typical solvents are those that are capable of solubilizing the rhodium complex and are not reactive to the hydroxyaldehydes that are produced in the hydroformylation step. Solvents may include an organic solvent having very low or minimal solubility in water. In certain embodiments, the hydroformylation reaction solvent is selected from C5-C20 aliphatic hydrocarbons, C6-C20 aromatic hydrocarbons, alcohols, ethers, or mixtures thereof. Without limitation, in certain embodiments, the hydroformylation reaction solvent is selected from toluene, cyclohexane, methyl t-butyl ether, xylenes or mixtures thereof. In embodiments, the hydroformylation reaction solvent is dry degassed toluene.

Typical hydroformylation reaction conditions that favor the formation of the linear HBA rather than branched HMPA reaction product are at lower temperature and moderate pressure conditions compared to typical commercial ethylene hydroformylation processes. In certain embodiments, hydroformylation reaction conditions comprise temperatures in the range of from 20 to 120° C., from 45 to 85° C., from 50 to 80° C., from 35° C. to 120° C., from 45° C. to 95° C., or from 50° C. to 70° C., or greater than or equal to 55° C., 60° C., or 65° C. In certain embodiments, hydroformylation reaction conditions comprise moderate pressures, for example in the range of from 137.9 kPa to 4136.85 kPa, from 206.84 kPa to 2757.90 kPa, from 275.79 kPa to 2068.42 kPA, from 689.48 kPa to 2757.9 kPa, or from 827.37 kPa to 2068.43 kPa.

The molar ratio of ethylene to carbon monoxide to hydrogen can vary, as long as the linear:branched ratio can be maintained at 10 or above. In embodiments, the molar ratio of ethylene:carbon monoxide:hydrogen ranges from (0.18-0.35):(2.7-4.1):(5-7).

The molar ratio of carbon monoxide to hydrogen ($CO:H_2$) can be about 1:1, although the ratio can vary considerably. In embodiments, the synthesis gas comprises a molar ratio of carbon monoxide to hydrogen in the range of from 0.5:1.5 to 1.5:0.5, from 0.8:1.2 to 0.9:1.1, or from 0.95:1.05 to 0.98:1.12, or greater than or equal to 1:1.

The molar ratio of ethylene to allyl alcohol can range from 1:10 to 1:2, if the reaction favors the formation of linear product over branched isomers, and an efficient water extraction is achieved. In embodiments, the molar ratio of ethylene to allyl alcohol ranges from 1:10 to 1:3. In embodiments, the molar ratio of ethylene to allyl alcohol ranges from 1:3 to 1:7, or from 1:3.38 to 1:6.56, or from 1:4 to 1:5. In some embodiments, the molar ratio of ethylene to allyl alcohol is about 1:4.37.

The partial pressure of CO may be within the range of 34.47 to 689.48 kPa. The partial pressure of hydrogen may be within the range of 275.79 to 1378.95 kPa. In embodiments, the hydroformylation reaction is conducted at these conditions until a predominance of the allyl alcohol has reacted, e.g. 60 to 99.9 mole percent, the products comprising primarily 4-hydroxybutyraldehyde with some branched reaction products.

In certain embodiments, the starting concentration of allyl alcohol on a combined hydroformylation reaction solvent (catalyst solution) and AA feed basis is calculated by $$\frac{\text{weight of } AA}{\text{weight of the solvent} + AA} \times 100\%$$

In embodiments, the concentration of AA is in the range of from 5 to 40 wt. % in the solution mixture. In embodiments, an allyl alcohol starting concentration on a hydroformylation reaction in the range of from 10 to 25 wt. % may be utilized.

The hydroformylation of allyl alcohol is carried out such that the concentration of CO in the liquid phase ($[CO]_{liq}$) is maintained above 4 mmols/liter (0.004 M) during the hydroformylation. The value of $[CO]_{liq}$ is defined in U.S. Pat. No. 6,225,509, the teachings of which are incorporated herein by reference for purposes not contrary to this disclosure. In certain embodiments, the liquid phase hydrogen:carbon monoxide molar ratio is in the range of from 10:1 to 1:2, or from 5:1 to 1:2.

Extraction of the catalyst is necessary in reducing the cost of production, as it allows the catalyst to be recycled back into the reaction after removal of the products. With the co-feeding of gaseous ethylene with liquid allyl alcohol, the catalyst in solvent can be readily separated from the hydroformylation products by water extraction, and therefore reducing the cost of production.

The water-to-feed ratio refers to the weight ratio of water to the hydroformylation effluent, composed of both catalyst solution and the aldehyde products that is introduced into the extraction column. The water-to-feed ratio can affect the efficiency of water extraction. In embodiments, the water-to-feed ratio ranges from 1:5 to 2:1, or 1:3 to 1:1, or 1:2 to 1:1.

The hydroformylation process of the present disclosure is performed at temperatures lower than used in conventional ethylene hydroformylation processes that are carried out at 90-120° C. The hydroformylation process of the present disclosure can be performed at 50-100° C. or in other embodiments at 50-80° C.

In one embodiment, the hydroformylation catalyst used in the hydroformylation process includes Rh and a ligand trans-1,2-bis(3,5-dimethylphenylphosphinomethyl) cyclobutane ("Ligand A" herein). In embodiments, the molar ratio of Rh to Ligand A ranges from 1:1 to 1:5. In certain embodiments, the molar ratio of Rh to Ligand A can be about 1:2.

Propionaldehyde is less polar than both HBA and its branched isomer, HMPA, and therefore has a higher affinity for the toluene phase, thereby reducing water extraction efficiency.

It has not been done to co-feed a liquid phase allyl alcohol with a gaseous phase ethylene to undergo the same hydroformylation reaction, because of the challenges presented and the difficult process control to reduce or eliminate the production of unwanted byproducts.

The following examples illustrate the range of ethylene co-feed amount, the effect of the amount of CO or $H_2$ on the hydroformylation, the effect of water-to-feed ratio on extraction efficiency, and the effect of propionaldehyde on the linear:branched (L:B) ratio of the products of AA hydroformylation, HBA:HMPA.

Example 1: Batch Hydroformylation

Gaseous ethylene and liquid allyl alcohol were co-fed utilizing syngas, a 50:50 hydrogen and carbon monoxide gas mixture into a hydroformylation reactor. A (1:1:1) gas mixture of ethylene, hydrogen and carbon monoxide procured from Praxair was used as the gaseous feed. This feed allowed the simultaneous introduction of the ethylene substrate with the reagent syngas. Rh-Ligand A was used as the catalyst. The first hydroformylation experiment used the gaseous feed (1:1:1) alone to establish an ethylene only baseline. The second experiment involved injection of allyl alcohol as a co-feed to demonstrate the production of both HBA, HMPA and PA.

The hydroformylation reactions were carried out using 1378.95 kPa of syngas, or in combination with ethylene, as the gaseous feed at 65° C. The catalyst comprises 200 ppm Rhodium and Ligand A with molar composition of [Rh]:[Ligand A]=1:2 and $[Rh]=4.3 \times 10^{-5}$ moles in a toluene solvent. The syngas consumption is shown in FIGS. 3A and B.

Figure 3A:
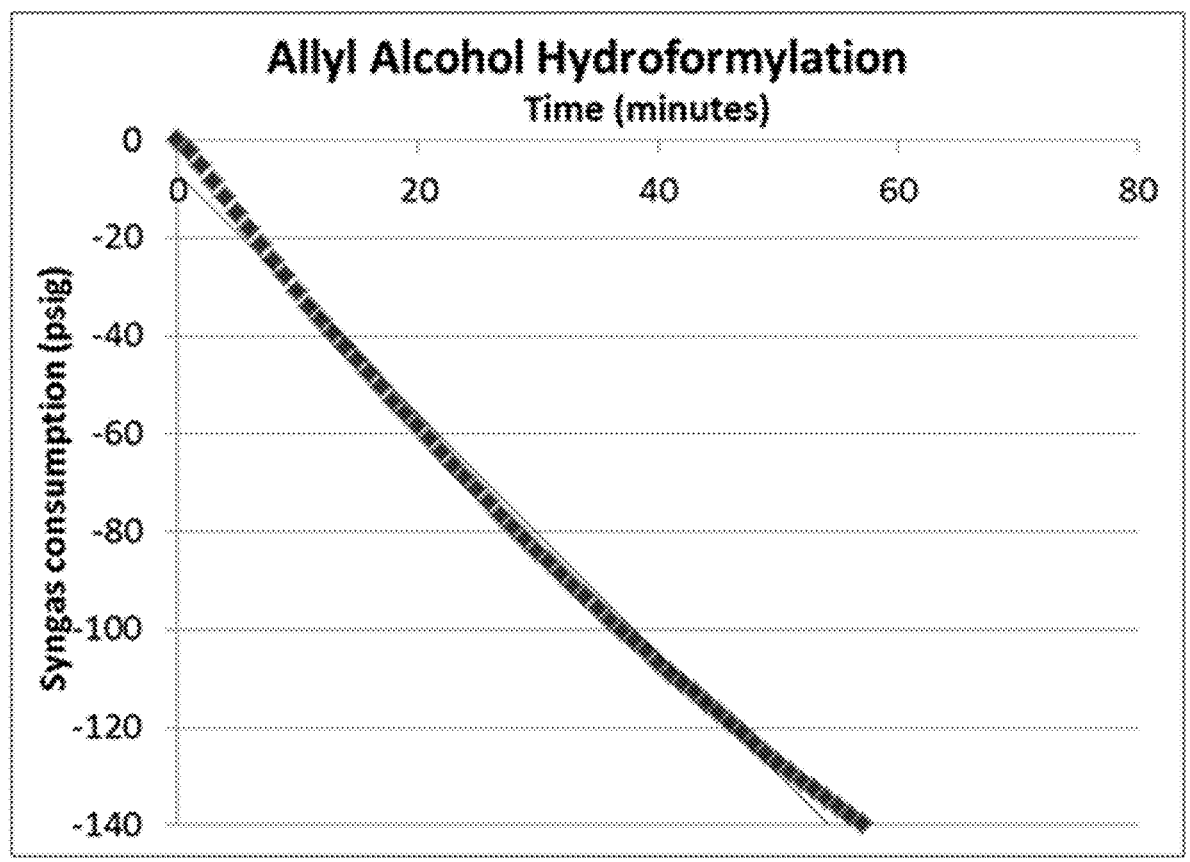
FIG. 3A provides a graph of syngas consumption in allyl alcohol hydroformylation.
Figure 3B:
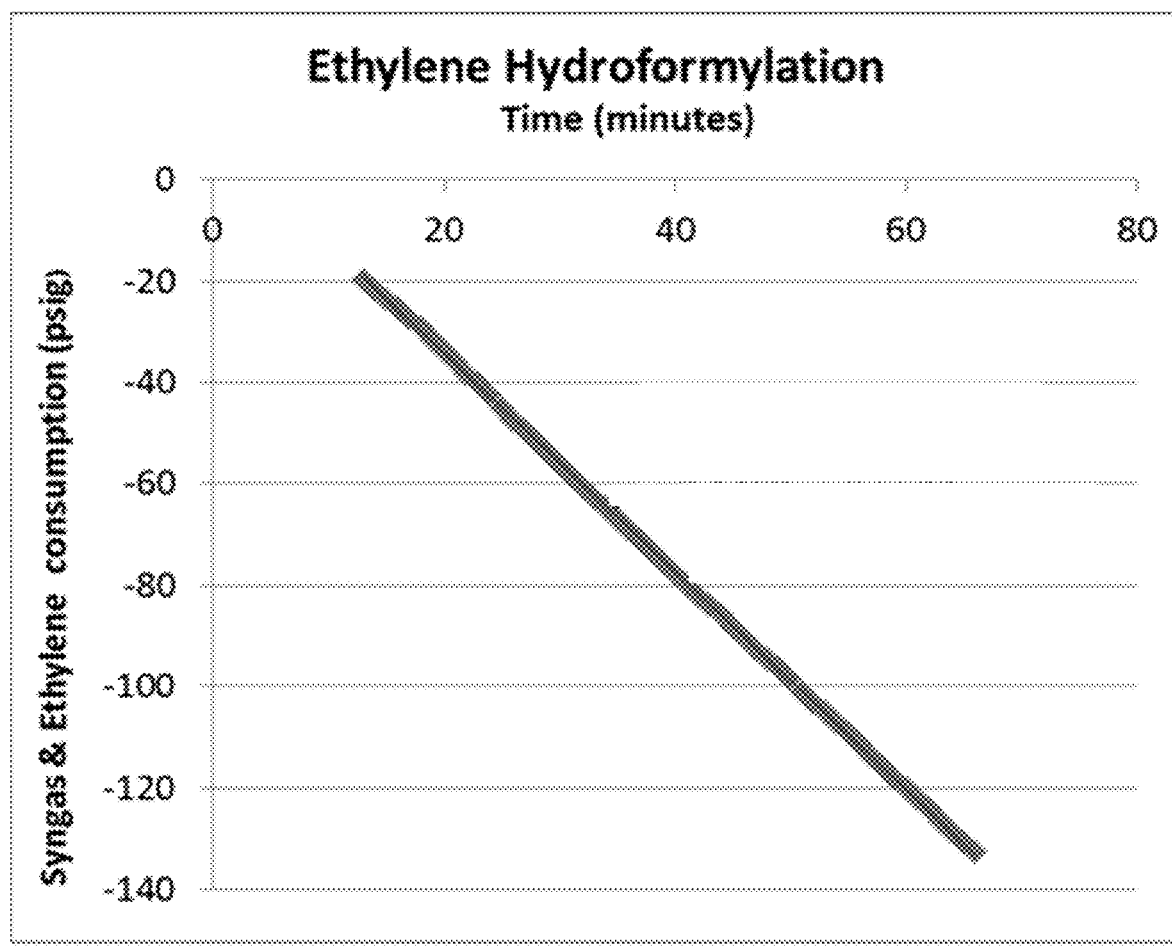
FIG. 3B provides a graph of syngas and ethylene consumption in ethylene hydroformylation.

As can be seen in FIGS. 3A and B, at 65° C. the independent hydroformylation AA and ethylene with the catalyst system results in similar kinetics. This indicated that both allyl alcohol and ethylene should be consumed in a similar manner if ran in the same reactor as co feeds.

Figure 4:
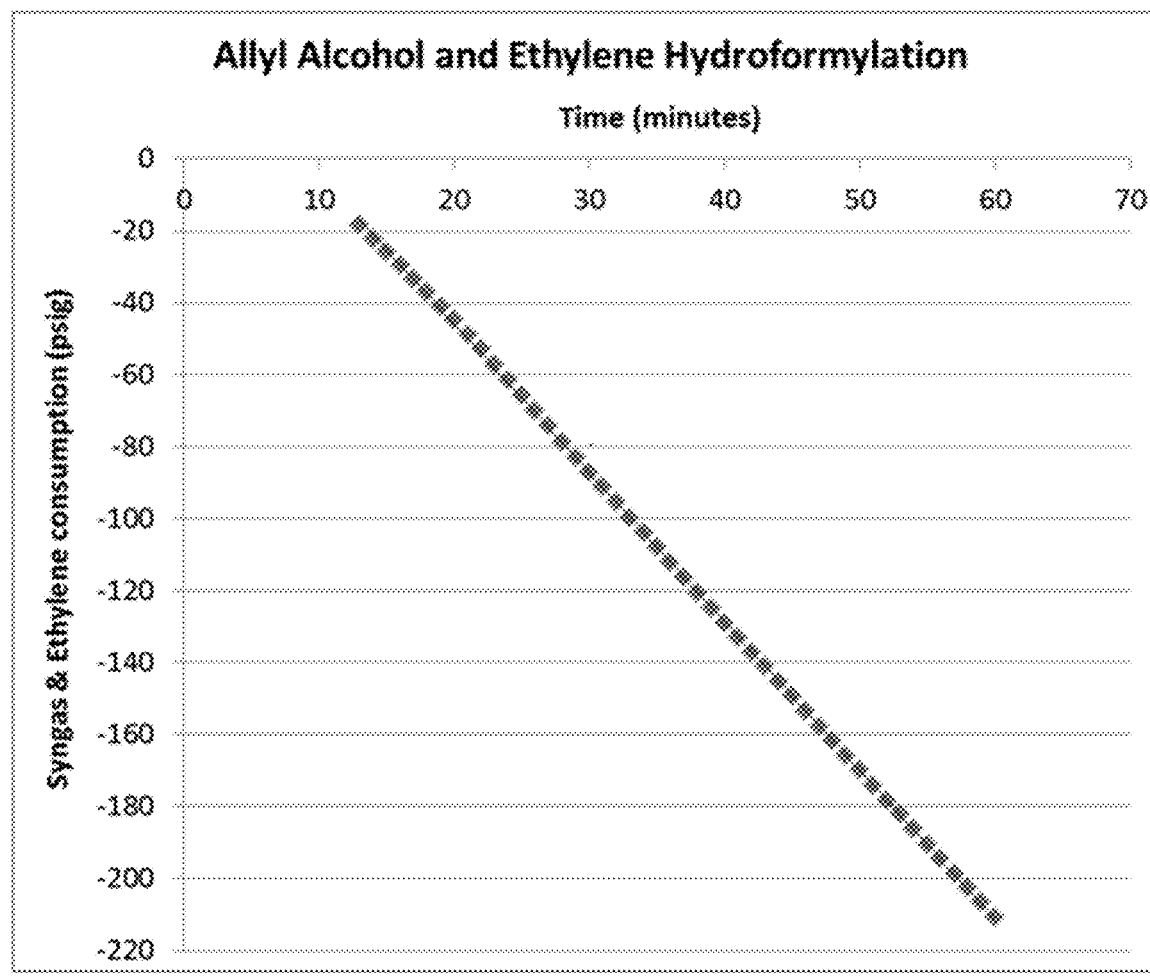
FIG. 4 provides a graph of syngas and ethylene consumption in allyl alcohol and ethylene hydroformylation.

The syngas and ethylene consumption of co-feeding allyl alcohol with ethylene is shown in FIG. 4. The hydroformylation results are summarized in Table 1.

TABLE 1

Batch Scale Hydroformylation Results

| Product/unreacted | Concentration (wt. %) | Comments |
|---|---|---|
| Allyl alcohol | 12 | Incomplete conversion because ethylene combined with syngas feed. |
| HBA (linear) | 45 | Linear: branched ratio = 10 |
| HMPA (branched) | 4.5 | |
| Propionaldehyde | 38 | Good ethylene conversion |
| Total | 99.5 | High selectivity to products: Few impurities |

As seen in Table 1, all the ethylene was converted to propionaldehyde only, as expected. More than 88 wt. % of allyl alcohol has been converted to either linear HBA or branched HMPA, wherein the linear:branched ratio is 10 to 1, indicating most of the product is the more desirable linear HBA over the branched HMPA. The high production of PA also indicates sufficient mixing of the gaseous ethylene co-feed to simultaneously undergo co-hydroformylation with AA.

Co-feeding gaseous ethylene with liquid allyl alcohol in the presence of the hydroformylation catalyst Rh-trans-1,2-bis(3,5-dimethylphenylphosphino-methyl)cyclobutane in a solvent can produce 10-to-1 molar ratio of linear-to-branched AA hydroformylation products, HBA and HMPA, and the ethylene hydroformylation product PA. Of equal importance, no increase in potential impurities such as (2-methyl-1,3-pentanediol) that could appear due to high PA content were observed. This demonstrates clear compatibility of the two feeds.

The use of the catalyst Rh-trans-1,2-bis(3,5-dimethylphenylphosphinomethyl) cyclobutane allows co-hydroformylation at low temperature, for example, in the range of from about 63 to 68° C., unlike commercial ethylene hydroformylation which uses Rh-phosphite ligands at temperatures in excess of 100° C. and as high as 120° C. This makes the commercial process energy intensive especially when coupled with the distillation of the propionaldehyde product from the hydroformylation catalyst solution.

Continuous Hydroformylation

Allyl alcohol feed was introduced at 68.3 g per hour as the feed rate, corresponding to 11% of the catalyst and substrate feed rate to the hydroformylation process. Ethylene gas was fed separately and mixed with the syngas components CO and $H_2$, which were fed independently, along with nitrogen added for balance to maintain an overall flow of 300 SLH (standard liter per hour). The gases were then combined and injected into the reactor through a single sparger. An equivalent flow of nitrogen was cut back or increased in order to maintain a total of 300 SLH whenever ethylene was added to the feed system or CO or $H_2$ feeds were adjusted at constant ethylene.

Varying the amount of ethylene feed, up to about 10 wt. % of the combined ethylene and allyl alcohol weight feed rate (or 18.6 mol feed ratio) is an effective reaction ratio. The concentration of ethylene is calculated as follows: (weight of ethylene/(weight of AA+weight of ethylene)). Here 10 wt. % of ethylene feed equals to a 18.6% mol feed ratio, as (7.52 g/(7.52+68.3 g)×100% corresponds to a 18.6% ((mols ethylene/mols. of AA+ mols ethylene)×100%).

The upper ethylene limit is based on loss of extraction efficiency, because when the ethylene feed goes above 10 wt. % water extraction efficiency is reduced due to the increase in propionaldehyde concentration increasing the miscibility of the toluene hydroformylation effluent with water resulting in failure to completely extract all the generated propionaldehyde from the hydroformylation effluent of catalyst solution and the generated aldehydes. Inadequate aqueous extraction results in some propionaldehyde remaining in and circulating back to the reactor with the toluene catalyst solution, which further reduces hydroformylation efficiency. Therefore, process control and the water extraction step contribute to the overall success of the production process.

Comparative Examples 1-2: Aa Feed

At 930.79 kPa, 65-68° C., an average AA feed rate of 80 cc/hr (68.3 g/hr), which corresponds to 11 wt. % feed concentration, was introduced into the reactor. The concentration of rhodium was 150-210 ppm, and the Ligand A:Rh mol ratio=1.5-1.8, the amount of 1,4-bis(diphenylphosphino)butane (DPPB) was 100 ppm, and the amount of triphenylphosphine (TPP) was about 0.1%.

For sufficient dissolved gas in liquid to ensure selective reaction to the desired products, $H_2$ feed rate was maintained between 111 and 131 SLH (equivalent to 13 to 16.5, mg-mol/L $[H_2]_{liq}$), and the CO feed rate was maintained between 53 and 68 SLH (equivalent to 10 to 15 mg-mol/L $[CO]_{liq}$). The gaseous mixture of CO and $H_2$ was maintained at 300 SLH with $N_2$ as the balance. The same consideration was applicable to all continuous examples herein.

The products were carried in the toluene catalyst solution, which was then fed to an extraction column. Chilled water was fed from the top of the column and extracted the aldehyde products from the toluene catalyst solution in a counter-current process. The toluene catalyst solution rose to the top of the column, and overflowed into a catalyst reservoir from which it was re-introduced into the hydroformylation reactor.

The aqueous aldehydes product solution exited the bottom of the extraction column and was further fed to a hydrogenation reactor. The hydrogenation catalyst was a molybdenum promoted sponge nickel, and during the hydrogenation reaction the linear 4-hydroxybutyraldehyde and branched 3-hydroxy-2-methylpropionadehyde were converted to 1,4-butanediol and 2-methyl-1,3-propanediol, respectively, whereas the side product propionaldehyde was converted to n-propanol.

The results for allyl alcohol feed only with variable CO at constant hydrogen feed at 63° C. is shown in Table 2. As shown, similar reaction results were achieved at CO feed rates of 68 and 63 SLH. Allyl alcohol conversion in hydroformylation is >99.9% with high selectivity to HBA and HMPA, >98.5% and low $C_3$<1% product selectivity. The low $C_3$ selectivity indicates low direct conversion to propionaldehyde from allyl alcohol (0.015 wt. %), while overall more than ~99 wt. % of allyl alcohol has been converted to either linear (BDO) or branched aldehyde (MPDiol®) after hydrogenation.

The results also show low aqueous rhodium losses at <50 ppb. This amount of loss corresponds to the rhodium dissolved in the toluene entrained in the aqueous phase exiting the extractor and therefore cannot be recycled back to the hydroformylation reactor.

TABLE 2

Continuous hydroformylation of AA only with variable CO at constant hydrogen at 63° C.

| | Gaseous Feed Rates (SLH) | | | Olefin Feed Rates | | | Hydroformylation | | | Extraction Conditions | | |
|---|---|---|---|---|---|---|---|---|---|---|---|---|
| | | | | Ethylene | Ethylene | Allyl Alcohol | Catalyst solution Recycle rate | Rh | AA Conversion | Catalyst soln + Products feed to extractor | Water feed | Water-to-feed ratio |
| | CO | $H_2$ | $N_2$ | (SLH) | (g/hr) | (g/hr) | (g/hr) | (ppm) | (wt. %) | (g/hr) | (g/hr) | |
| Com.Ex. 1 | 68 | 131 | 101 | 0 | 0 | 68.3 | 554 | 174 | 99.9 | 658.49 | 330 | 0.50 |
| Com.Ex. 2 | 63 | 131 | 106 | 0 | 0 | 68.3 | 554 | 173 | 99.9 | 658.49 | 330 | 0.50 |

| | n-Pr & PA make in hydroformylation | | Calculated Hydrogenation Selectivities | | | | Observed Selectivities (GC Analysis) | | | |
|---|---|---|---|---|---|---|---|---|---|---|
| | | | | BDO | MPDiol® | | | BDO | MPDiol® | |
| | n-Pr (wt. %) | PA (wt. %) | $C_3$ sel. (wt. %) | Sel. (wt. %) | Sel. (wt. %) | BDO/MPDiol® | $C_3$ Sel (wt. %) | Sel (wt. %) | Sel. (wt. %) | BDO/MPD |
| Com.Ex. 1 | 0.08 | 0.02 | 0.32 | 90.60 | 9.06 | 10.00 | 0.66 | 89.80 | 8.72 | 10.30 |
| Com.Ex. 2 | 0.08 | 0.01 | 0.32 | 90.60 | 9.06 | 10.00 | 0.64 | 89.28 | 8.66 | 10.31 |

Examples 2-5: Hydrogen Feed

Hydrogen gas feed was supplied between 111 and 160 SLH at 65° C., with otherwise the same reaction condition as Comparative Example 1. All examples showed comparable performance in terms of AA conversion (99.9%), $C_3$ selectivity (0.58-0.67 wt. %), BDO selectivity (89.02-90.57 wt. %), MPDiol® selectivity (8.78-8.93 wt. %), and n-propanol/propionaldehyde production (0.09/0.02 wt %). While theoretically, average n-propanol concentration in hydroformylation of allyl alcohol is 0.1 wt. % (0.32% selectivity), the results from Examples 2-5 doubles the results to about 0.2 wt. % (1.8 mmol/hr, about 0.64% selectivity). This, however, still shows that very little (~0.2 wt. %) of propionaldehyde is generated directly from allyl alcohol conversion in hydroformylation. 0.2 wt. % is negligible in practical sense.

Further, the lower loss of catalyst during water extraction reduces the overall cost. Here the loss of rhodium catalyst was all below 60 ppb, comparable to Comparative Examples 1-2, indicating a wide operating window for the $H_2$ feed rate (concentration) with stable performance maintained and no negative impact to the system.

TABLE 2A

Continuous hydroformylation of AA only with variable Hydrogen at constant CO at 65° C.

| | Gaseous Feed Rates (SLH) | | | Olefin Feed Rates | | | Hydroformylation | | | Extraction Conditions | | |
|---|---|---|---|---|---|---|---|---|---|---|---|---|
| | | | | Ethylene | Ethylene | Allyl Alcohol | Catalyst solution Recycle rate | Rh | AA Conversion | Catalyst soln + Products feed to extractor | Water feed | Water-to-feed ratio |
| | CO | $H_2$ | $N_2$ | (SLH) | (g/hr) | (g/hr) | (g/hr) | (ppm) | (wt. %) | (g/hr) | (g/hr) | |
| Com.Ex. 3 | 63 | 121 | 116 | 0 | 0 | 68.3 | 554 | 165 | 99.9 | 658.49 | 330 | 0.50 |
| Com.Ex. 4 | 63 | 111 | 126 | 0 | 0 | 68.3 | 554 | 190 | 99.9 | 658.49 | 330 | 0.50 |
| Com.Ex. 5 | 63 | 161 | 77 | 0 | 0 | 68.3 | 554 | 180 | 99.9 | 658.49 | 330 | 0.50 |

| | n-Pr & PA make in hydroformylation | | Calculated Hydrogenation Selectivities | | | | Observed Selectivities (GC Analysis) | | | |
|---|---|---|---|---|---|---|---|---|---|---|
| | | | | BDO | MPDiol® | | | BDO | MPDiol® | |
| | n-Pr (wt. %) | PA (wt. %) | $C_3$ sel. (wt. %) | Sel. (wt. %) | Sel. (wt. %) | BDO/MPDiol® | $C_3$ Sel (wt. %) | Sel (wt. %) | Sel. (wt. %) | BDO/MPD |
| Com.Ex. 3 | 0.09 | 0.02 | 0.32 | 90.60 | 9.06 | 10.00 | 0.62 | 90.34 | 8.83 | 10.23 |
| Com.Ex. 4 | 0.09 | 0.02 | 0.32 | 90.60 | 9.06 | 10.00 | 0.62 | 90.4 | 8.93 | 10.12 |
| Com.Ex. 5 | 0.09 | 0.02 | 0.32 | 90.60 | 9.06 | 10.00 | 0.58 | 90.57 | 8.78 | 10.32 |

Examples 6-13: Ethylene Co-Feed for Continuous Reaction

Examples 6-9 illustrate the ethylene feed at different flow rates that increases the production of n-propanol while maintaining linear: branched product ratio of 10 for the AA to BDO main process. Ethylene feed rate was varied between 4 and 8 SLH, and CO was maintained at 68 SLH to ensure sufficient supply, except for Example 6 where CO was kept at 63 SLH to compare with Example 4. Examples 10-13 varies the CO feed rates from 53 to 85 SLH, while maintaining ethylene feed rate at 6 SLH. Other conditions were the same as Comparative Example 1. The result is shown in Table 3.

9.71. Here the selectivity to the linear product (BDO) decreases as the branched MPDiol® increases when CO feed rate is below that in Example 13, especially when ethylene is co-fed with AA. The branched pathway is also the path that produces propionaldehyde and consequently n-propanol when allyl alcohol is the only feed.

Specifically regarding $C_3$ selectivity, the results show increased $C_3$ production (10.30 wt. % in Ex. 6 vs. 0.66 wt. % in Comparative Example 1) while maintaining the linear: branched product ratio of the primary AA to BDO process at 10. The fact that examples 6 through 8 essentially show the same amount of n-propanol directly produced in hydroformylation, ~0.08 wt. % as in Comp Ex 1 or 2 shows that there is no increase in direct hydrogenation of AA to

TABLE 3

Co-Feeding of Ethylene and AA in Continuous Hydroformylation

| | Gaseous Feed Rates (SLH) | | | Olefin Feed Rates | | Allyl Alcohol | Feed Ratio Ethylene (mol) % of | Hydroformylation | | Extraction Conditions | | |
|---|---|---|---|---|---|---|---|---|---|---|---|---|
| Examples | CO | $H_2$ | $N_2$ | Ethylene (SLH) | Ethylene (g/hr) | (g/hr) | total feed | Rh (ppm) | AA Conversion (wt. %) | Water-to-feed ratio | Interfacial tension (dynes/cm) | Rh loss in water (ppb) |
| Ex. 6 | 63 | 131 | 102 | 4 | 5.01 | 68.3 | 13.19 | 155 | 99.9 | 0.49 | | 23 |
| Ex. 7 | 68 | 131 | 97 | 4 | 5.01 | 68.3 | 13.19 | 191 | 99.9 | 1.0 | | 41 |
| Ex. 8 | 68 | 131 | 95 | 6 | 7.52 | 68.3 | 18.57 | 192 | 99.9 | 0.50 | | 40 |
| Ex. 9 | 68 | 131 | 93 | 8 | 10.02 | 68.3 | 23.3 | 175 | 99.9 | 0.50 | 4.09 | 88 |
| Ex. 10 | 73 | 131 | 90 | 6 | 7.52 | 68.3 | 18.57 | 187 | 99.9 | 0.50 | | 37 |
| Ex. 11 | 85 | 131 | 78 | 6 | 7.52 | 68.3 | 18.57 | 171 | 99.9 | 0.50 | | 40 |
| Ex. 12 | 58 | 131 | 105 | 6 | 7.52 | 68.3 | 18.57 | 179 | 99.9 | 0.50 | | 48 |
| Ex. 13 | 53 | 131 | 110 | 6 | 7.52 | 68.3 | 18.57 | 187 | 99.9 | 0.50 | | 46 |

| | Calculated Hydrogenation Selectivities | | | | | | Observed Selectivities (GC Analysis) | | | |
|---|---|---|---|---|---|---|---|---|---|---|
| | n-Pr & PA make in hydroformylation | | $C_3$ sel. Ethylene only | BDO Sel. | MPDiol® Sel. | | | $C_3$ Sel combined | BDO Sel | MPDiol® Sel. | |
| Examples | n-Pr (wt. %) | PA (wt. %) | (wt. %) | (wt. %) | (wt. %) | BDO/ MPDiol® | (wt. %) | (Wt %) | (wt. %) | BDO/ MPD |
| Ex. 6 | 0.08 | 3.03 | 9.24 | 82.51 | 8.25 | 10 | 10.30 | 80.10 | 7.82 | 10.24 |
| Ex. 7 | 0.08 | 4.38 | 9.24 | 82.51 | 8.25 | 10 | 9.21 | 81.15 | 8.02 | 10.12 |
| Ex. 8 | 0.08 | 5.39 | 13.25 | 78.86 | 7.89 | 10 | 14.00 | 77.30 | 7.74 | 9.99 |
| Ex. 9 | 0.11 | 9.39 | 16.92 | 75.53 | 7.55 | 10 | 17.30 | 74.26 | 7.48 | 9.92 |
| Ex. 10 | 0.177 | 7.02 | 13.25 | 78.86 | 7.89 | 10 | 13.77 | 77.70 | 7.72 | 10.06 |
| Ex. 11 | 0.172 | 6.86 | 13.25 | 78.86 | 7.89 | 10 | 13.77 | 77.70 | 7.71 | 10.08 |
| Ex. 12 | 0.197 | 6.86 | 13.25 | 78.86 | 7.89 | 10 | 14.20 | 77.19 | 7.73 | 9.99 |
| Ex. 13 | 0.210 | 7.11 | 13.25 | 78.86 | 7.89 | 10 | 14.77 | 76.50 | 7.88 | 9.71 |

The results in Table 3 are of co-feeding up to 23.3 mol % ethylene with 68.3 g/hr of allyl alcohol, (76.7 mol % of total feed). Under all the test conditions, quantitative AA conversion >99.9% is observed with high selectivity to BDO and MPDiol® maintained. This again shows that co-feeding liquid allyl alcohol with gaseous ethylene successfully produces BDO/MPDiol® as well as n-propanol. Specifically, in terms of BDO/MPDiol® ratio, Examples 6-12 show the ratio above 9.9~10, indicating no significant increase in the branched product pathway. A requirement for success is to maintain the BDO/MPDiol® ratio above 10, especially within a system having four reactants in two phases and four possible products. The results show by maintaining the ethylene co-feed at 7.52 g/hr=<9.92 wt. % the linear: branched ratio of the AA to BDO process is maintained at above 10, which has not been previously demonstrated.

Example 13 provides a lower limit of CO feed rate, which resulted in a significantly reduced linear: branched ratio of propanol in the hydroformyaltion stage when ethylene is co-fed. Those versed in the art will appreciate that the result implies that the pathway from AA to the branched HMPA product which also produces both PA and n-propanol is not favored or enhanced when ethylene is co-fed with AA. This result conforms with the observed maintenance of the BDO: MPDiol® ratio at 10 following hydrogenation of the hydroformylation products.

Comparison of the calculated $C_3$ selectivity based on ethylene feed only and the observed combined selectivity (ethylene only+baseline for AA only feed) shows good agreement with a quantitative process. Thus in Ex 6, ethylene only n-Pr selectivity is 9.24 wt. % while Ex 2 the baseline is 0.64 wt. % giving a combined total of 9.88 wt. % selectivity, ~96% of the observed 10.3 wt. % based on GC analysis. This is within expected error for GC analysis. Similarly (Ex. 8/10/11/12 all have calculated 13.25 wt. % n-Pr selectivity for ethylene only feed and an observed combined n-Pr totals of 14.00/13.77/13.77/14.20 wt. % selectivities. Again all observed values are within +−2% of the calculated ethylene only, (13.25 wt. %)+baseline n-Pr~ (0.65 wt. %), giving a combined n-Pr total of 13.9 wt. %. This confirms successful co-feeding ethylene with AA to yield n-Pr and BDO/MPDiol® without significant, negative impact on the ratio of the BDO to MPDiol® of approximately 10. Example 9, showing the upper limit of ethylene co-feed for effective extraction again, still shows quantitative recovery of products, calculated ethylene only n-Pr, 16.92 wt. %+0.65 wt. % baseline giving combined n-Pr of 17.57 wt. % selectivity compared to the GC based 17.3 wt. %, again within experimental error.

Example 9, 14 and 15: Extraction Efficiency

To determine the effect of water-to-feed ratio on extraction efficiency, conditions according to Example 9 were repeated, except the water-to-feed ratio was gradually increased from 0.5 to 1.0. The results are shown in Table 4.

to the calculated ethylene only 16.92 wt. %+baseline 0.65 wt. %/(17.57 wt. % selectivity). This again shows good agreement between the theoretical (calculated) and observed selectivities based on GC analysis.

Taking Examples 8-12 together, co-feeding 18.6 mol % ethylene with allyl alcohol with a water-to-feed extraction ratio of 0.5 shows an operation range with low rhodium catalyst losses (<50 ppb), matching the performance of the main, allyl alcohol feed only process. Examples 6 and 7 show that additional ethylene may be added as the extraction ratio of 0.5 outperforms the ratio of 1.0 in terms of rhodium loss (cf. 23 vs. 41 ppb). Without being bound to theory, Example 7 may have higher rhodium loss despite the higher water ratio due to having more rhodium in the reactor. Nevertheless, the losses are still below 50 ppb.

Also, keeping the CO feed rate at 58 SLH (12.24 mg-mol/L or above) ensures that the linear: branch ratio of at least 10 is maintained for the primary AA to BDO/MPDiol® process when ethylene is co-feed. As discussed previously,

TABLE 4

Effect of Water-to-Feed ratio on Extraction Efficiency

| Examples | Gaseous Feed Rates (SLH) | | | Olefin Feed Rates | | | Feed Ratio | Hydroformylation | | Extraction Conditions | | | |
|---|---|---|---|---|---|---|---|---|---|---|---|---|---|
| | CO | $H_2$ | $N_2$ | Ethylene (SLH) | Ethylene (g/hr) | Allyl Alcohol (g/hr) | Ethylene/ AA (mol) % | Rh (ppm) | AA Conversion (wt. %) | Water-to-feed ratio | Interfacial tension (dynes/cm) | PA in recycled catalyst | Rh loss in water (ppb) |
| Ex. 9 | 68 | 131 | 93 | 8 | 10.02 | 68.3 | 30.38 | 175 | 99.9 | 0.50 | 4.09 | 5.10% | 88 |
| Ex. 14 | 68 | 131 | 93 | 8 | 10.02 | 68.3 | 30.38 | 180 | 99.9 | 0.70 | 4.41 | 3.00% | 31 |
| Ex. 15 | 68 | 131 | 93 | 8 | 10.02 | 68.3 | 30.38 | 177 | 99.9 | 1.00 | 6.00 | 1.50% | 36 |

| Experiment | Calculated Hydrogenation Selectivities | | | | | Observed Selectivities (GC Analysis) | | | |
|---|---|---|---|---|---|---|---|---|---|
| | n-Pr & PA make in hydroformylation | | C3 sel. Ethylene only | BDO Sel. | MPDiol® Sel. | BDO/ MPDiol® | C3 Sel Combined | BDO Sel | MPDiol® Sel. | BDO/ MPD |
| | n-Pr (wt. %) | PA (wt. %) | (wt. %) | (wt. %) | (wt. %) | | (wt. %) | (Wt %) | (wt. %) | |
| Ex. 9 | 0.11 | 9.39 | 16.92 | 75.33 | 7.53 | 10 | 17.30 | 74.26 | 7.48 | 9.92 |
| Ex. 14 | 0.11 | 9.39 | 16.92 | 75.33 | 7.53 | 10 | 17.97 | 73.95 | 7.27 | 10.13 |
| Ex. 15 | 0.11 | 9.39 | 16.92 | 75.33 | 7.53 | 10 | 17.40 | 74.40 | 7.27 | 10.23 |

As shown in Table 4, the lowest water-to-feed ratio in Example 9 also results in the least effective extraction, with Rh loss the highest (88 ppb), indicating some toluene being entrained in the aqueous phase exiting the extraction column. This is also confirmed by the least interfacial tensions (4.09 dynes/cm). Additionally, the highest retention of propionaldehyde in the catalyst solution post-aqueous extraction also makes it least favorite for reintroducing the catalyst into the reactor.

Therefore, when the water-to-feed ratio was increased to 0.7 (Example 14) and 1.0 (Example 15), the extraction efficiency was improved, and the rhodium loss was reduced. However, these higher water-to-feed ratios, (Ex. 14 and 15) are not desirable in commercial applications as energy would be required to remove the excess water in the purification of the hydrogenation products. For this reason, a process with a water to feed ratio of =<0.5 is more desirable.

In terms of $C_3$ production, all three examples show expected actual $C_3$ selectivities within the range of the calculated, (Ex. Sep. 14, 2015=17.40/17.97/17.30 compared in example 13 the CO feed rate of 53 SLH shows the decrease in L:B ratio of 9.7 when the CO concentration in the system is too low to maintain selectivity of the primary AA to BDO/MPDiol® process.

It is shown that co-feeding gaseous ethylene with liquid allyl alcohol in hydroformylation reaction does not negatively affect the selectivities of the linear product over its branched isomer, for the primary AA to BDO/MPDiol® process while also achieving high n-propanol production. This disclosure demonstrates the benefit of combining allyl alcohol and ethylene hydroformylation without the need for new reactors or extraction equipment, while obtaining quantitative n-propanol production along with the primary process BDO/MPDiol® products. Also, the reaction can be carried out at a lower temperature to reduce energy cost while maintaining high conversion rate. The added benefit of n-propanol production has wide applications.

While certain embodiments have been shown and described, modifications thereof can be made by one skilled in the art without departing from the teachings of this disclosure.

Numerous other modifications, equivalents, and alternatives will become apparent to those skilled in the art once the above disclosure is fully appreciated. It is intended that the following claims be interpreted to embrace such modifications, equivalents, and alternatives where applicable. Accordingly, the scope of protection is not limited by the description set out above but is only limited by the claims which follow, that scope including equivalents of the subject matter of the claims.

What is claimed is:

1. A method comprising the steps of:
   a) introducing a gaseous mixture of ethylene, carbon monoxide and hydrogen into a reactor in the presence of a hydroformylation catalyst in a solvent;
   b) introducing liquid allyl alcohol (AA) into the reactor; and
   c) carrying out hydroformylation reaction at a temperature between 50 and 100° C. to obtain hydroformylation products, wherein the hydroformylation products include 4-hydroxybutyraldehyde, 3-hydroyx-2-methylpropionaldehyde, propionaldehyde or a combination thereof.

2. The method of claim 1, wherein the molar ratio of ethylene to allyl alcohol ranges from 1:3 to 1:7.

3. The method of claim 1, wherein the molar ratio of ethylene to allyl alcohol ranges from 1:4 to 1:5.

4. The method of claim 1, wherein the amount of allyl alcohol ranges between 10 and 25 wt. % concentration in the solvent, calculated by $$\frac{\text{weight of } AA}{\text{weight of the solvent} + AA} \times 100\%.$$

5. The method of claim 1, wherein molar ratio of ethylene:carbon monoxide:hydrogen is (0.18-0.35):(2.7-4.1):(5-7).

6. The method of claim 1, wherein the molar ratio of ethylene:carbon monoxide:hydrogen is about 1:13:22.

7. The method of claim 1, wherein in step c) the hydroformylation reaction is carried out at a moderate pressure in the range of from about 137.9 kPa to about 1378.95 kPa.

8. The method of claim 1, wherein in step c) the hydroformylation reaction is carried out at a moderate pressure in the range of from about 689.48 kPa to about 1034.21 kPa.

9. The method of claim 1, wherein in step c) the hydroformylation reaction is carried out at a moderate pressure in the range of from about 896.32 kPa to about 965.27 kPa.

10. The method of claim 1, wherein the hydroformylation catalyst is a mixture of rhodium and a ligand selected from the group consisting of trans-1,2-bis(3,5-trimethylphenylphosphinomethyl) cyclobutane (Ligand A), 1,4-bis(diphenylphosphinobutane) (DPPB), triphenylphosphine (TPP), bidentate biphosphate, and combinations thereof.

11. The method of claim 10, wherein the molar ratio of rhodium to Ligand A ranges from 1:1 to 1:5.

12. The method of claim 10, wherein the molar ratio of rhodium to Ligand A is about 1:2.

13. The method of claim 10, wherein the hydroformylation catalyst is a mixture of rhodium, Ligand A, DPPB and TPP.

14. The method of claim 13, wherein the molar ratio of rhodium:Ligand A:DPPB:TPP is about 1:2:0.1:2.

15. The method of claim 10, wherein the rhodium is present in an amount of 50 to 500 ppm.

16. The method of claim 1, wherein in step c) the temperature is between 50 and 80° C.

17. The method of claim 1, further comprising the step of: separating the products from the solvent and the catalyst by water extraction.

18. The method of claim 17, wherein a water-to-feed ratio ranges from 1:5 to 2:1.

19. The method of claim 1, further comprising the step of:
   (d) treating the hydroformylation products include 4-hydroxybutyraldehyde, 3-hydroxy-2-methylpropionaldehyde, and propionaldehyde with a Ni hydrogenation catalyst to produce a hydrogenation product, wherein the hydrogenation product includes, 1,4-butanediol, 2-methyl-1,3-propanediol, propanol or a combination thereof.

20. The method of claim 19, wherein the hydroformylation catalyst is a mixture of rhodium and a ligand selected from the group consisting of trans-1,2-bis(3,5-trimethylphenylphosphinomethyl) cyclobutane (Ligand A), 1,4-bis(diphenylphosphinobutane) (DPPB), triphenylphosphine (TPP), bidentate biphosphate, and combinations thereof.

* * * * *

UNITED STATES PATENT AND TRADEMARK OFFICE
CERTIFICATE OF CORRECTION

| | | |
|---|---|---|
| PATENT NO. | : 11,370,737 B2 | Page 1 of 1 |
| APPLICATION NO. | : 17/480265 | |
| DATED | : June 28, 2022 | |
| INVENTOR(S) | : White et al. | |

It is certified that error appears in the above-identified patent and that said Letters Patent is hereby corrected as shown below:

In the Claims

In Column 17, Claim 1, Line 20, delete "hydroyx" and insert -- hydroxy- --, therefor Signed and Sealed this
Sixteenth Day of January, 2024

Katherine Kelly Vidal
Director of the United States Patent and Trademark Office